United States Patent
Bai et al.

(10) Patent No.: US 11,691,139 B2
(45) Date of Patent: Jul. 4, 2023

(54) ACID/METAL BIFUNCTIONAL CATALYST SYSTEMS PRODUCED WITH CARBON COATINGS

(71) Applicant: ExxonMobil Technology and Engineering Company, Annandale, NJ (US)

(72) Inventors: Chuansheng Bai, Phillipsburg, NJ (US); Majosefina Cunningham, Whitehall, PA (US); Jihad M. Dakka, Whitehouse Station, NJ (US); Preeti Kamakoti, Berkeley Heights, NJ (US); Aruna Ramkrishnan, Bridgewater, NJ (US); Anjaneya S. Kovvali, Herndon, VA (US); Anita S. Lee, Spring, TX (US)

(73) Assignee: ExxonMobil Technology and Engineering Company, Annandale, NJ (US)

(*) Notice: Subject to any disclaimer, the term of this patent is extended or adjusted under 35 U.S.C. 154(b) by 310 days.

(21) Appl. No.: 16/947,706

(22) Filed: Aug. 13, 2020

(65) Prior Publication Data

US 2021/0046470 A1    Feb. 18, 2021

Related U.S. Application Data

(60) Provisional application No. 62/886,987, filed on Aug. 15, 2019.

(51) Int. Cl.
*B01J 37/08* (2006.01)
*B01J 37/02* (2006.01)
(Continued)

(52) U.S. Cl.
CPC ............. *B01J 37/084* (2013.01); *B01J 21/18* (2013.01); *B01J 23/80* (2013.01); *B01J 29/40* (2013.01);
(Continued)

(58) Field of Classification Search
CPC . B01J 37/084; B01J 21/18; B01J 23/80; B01J 29/40; B01J 33/00; B01J 37/0219; B01J 37/0221; B01J 37/04; B01J 37/10
(Continued)

(56) References Cited

U.S. PATENT DOCUMENTS

| 4,423,155 A | 12/1983 | Bell et al. |
| 5,218,003 A | 6/1993 | Lewnard et al. |

(Continued)

FOREIGN PATENT DOCUMENTS

| CN | 101485983 | * 7/2009 | ............... B01J 23/72 |
| CN | 101485983 A | 7/2009 | |

(Continued)

OTHER PUBLICATIONS

Bae, J.-W., et al., "Coproduction of Methanol and Dimethyl Ether from Biomass-Derived Syngas on a Cu—ZnO—Al2O3/γ-Al2O3 Hybrid Catalyst", Energy and Fuels, vol. 22, No. 1, pp. 223-230 (2008).

(Continued)

*Primary Examiner* — Patricia L. Hailey
(74) *Attorney, Agent, or Firm* — Shook, Hardy & Bacon L.L.P.

(57) ABSTRACT

A method of producing bifunctional catalyst systems that include a carbon-coated metal catalyst may comprise: coating a metal catalyst particle with a carbon-containing small molecule to produce a coated metal catalyst particle; carbonizing the carbon-containing small molecule on the coated metal catalyst particle to produce a carbon-coated (Continued)

metal catalyst particle; and mixing the carbon-coated metal catalyst particle with an acid catalyst particle to produce an acid/metal bifunctional catalyst system. Further, a method of producing bifunctional catalyst systems that include a carbon-coated acid catalyst may be similarly performed by coating a metal catalyst particle with a carbon-containing small molecule to produce a coated metal catalyst particle; carbonizing the carbon-containing small molecule on the coated metal catalyst particle to produce a carbon-coated metal catalyst particle; and mixing the carbon-coated metal catalyst particle with an acid catalyst particle to produce an acid/metal bifunctional catalyst system.

29 Claims, 5 Drawing Sheets

(51) Int. Cl.
    *B01J 37/04* (2006.01)
    *C07C 41/01* (2006.01)
    *B01J 33/00* (2006.01)
    *B01J 21/18* (2006.01)
    *B01J 29/40* (2006.01)
    *B01J 37/10* (2006.01)
    *B01J 23/80* (2006.01)

(52) U.S. Cl.
    CPC ........... *B01J 33/00* (2013.01); *B01J 37/0219* (2013.01); *B01J 37/0221* (2013.01); *B01J 37/04* (2013.01); *B01J 37/10* (2013.01); *C07C 41/01* (2013.01)

(58) Field of Classification Search
    USPC ....... 502/104, 182, 302, 305, 308, 312, 313,
                  502/317, 320, 323–327, 330, 332, 346,
                  502/348, 351, 355
    See application file for complete search history.

(56) References Cited

U.S. PATENT DOCUMENTS

| | | | | |
|---|---|---|---|---|
| 6,069,107 | A * | 5/2000 | Kuznetsov | .......... H01M 4/8615 427/249.1 |
| 2012/0157554 | A1 | 6/2012 | Okuyama et al. | |
| 2013/0030224 | A1 * | 1/2013 | Kim | .......... B01J 23/74 568/885 |
| 2013/0211147 | A1 | 8/2013 | Cheiky et al. | |
| 2017/0297986 | A1 * | 10/2017 | Lee | .......... C01B 3/34 |

FOREIGN PATENT DOCUMENTS

| | | | | | |
|---|---|---|---|---|---|
| CN | | 104069856 | * | 10/2014 | .............. B01J 23/44 |
| CN | | 104646049 | * | 5/2015 | .............. B01J 23/80 |
| CN | | 104646049 | A | 5/2015 | |
| CN | | 104069856 | B | 4/2016 | |
| CN | 10 | 6536045 | * | 3/2017 | .............. B01J 21/12 |
| JP | | 2003-038957 | * | 2/2003 | .............. B01J 23/80 |
| JP | | 2003-38957 | A | 2/2003 | |
| WO | | 2005/046855 | A2 | 5/2005 | |

OTHER PUBLICATIONS

Kamata, H., et al., "Steam Reforming of Dimethyl Ether over Cu/ZnO/ZrO2 and γ-Al2O3 Mixed Catalyst Prepared by Extrusion", Journal of the Japan Petroleum Institute, vol. 51, No. 3, pp. 157-164 (2008).
Gentzen, M., et al., "Bifunctional catalysts based on colloidal Cu/Zn nanoparticles for the direct conversion of synthesis gas to dimethyl ether and hydrocarbons," Applied Catalysis A: General, vol. 557, pp. 99-107 (Year: 2018).
Gentzen, M., et al., "Bifunctional hybrid catalysts derived from Cu/Zn-based nanoparticles for single-step dimethyl ether synthesis", Catalysis Science & Technology, vol. 6, pp. 1-10 (2016).
Zhang, Q., et al., "Improvement of a Mesh-Type Cu/Ni/γ-Al2O3/Al Catalyst for Steam Reforming of Dimethyl Ether by Metal (Fe, Zn or La) Addition for CO in Situ Removal", Modem Research in Catalysis, vol. 7, pp. 1-16 (Jan. 31, 2018).
Non-Final Office Action dated Apr. 11, 2022 in U.S. Appl. No. 16/993,219, 12 pages.
Non-Final Office Action dated Jul. 21, 2022 in U.S. Appl. No. 16/947,699, 12 pages.
Non-Final Office Action dated Aug. 4, 2022 in U.S. Appl. No. 16/947,704, 14 pages.
Non-Final Office Action dated Aug. 23, 2022 in U.S. Appl. No. 16/947,701, 10 pages.
Notice of Allowance dated Oct. 21, 2022 in U.S. Appl. No. 16/993,219, 9 pages.
Final Office Action dated Jan. 12, 2023 in U.S. Appl. No. 16/947,704, 16 pages.

* cited by examiner

ACID/METAL BIFUNCTIONAL CATALYST SYSTEMS PRODUCED WITH CARBON COATINGS

CROSS REFERENCE TO RELATED APPLICATIONS

This application claims priority to U. S. Provisional Application Ser. No. 62/886,987 filed Aug. 15, 2019, which is herein incorporated by reference in its entirety.

FIELD

The present disclosure relates to catalysts for direct conversion of syngas to dimethyl ether.

BACKGROUND

Various processes have been proposed for producing dimethyl ether from natural gas.

One such process involves co-feeding natural gas with an enriched oxygen stream to an autothermal reformer to produce syngas. Dimethyl ether may then be produced in a two-stage process. In a first stage, methanol is synthesized from the syngas. In the methanol synthesis step, un-reacted gas from the methanol synthesis reactor may be recycled back to the reactor, thereby acting as a syngas quench cooler. The recycle ratio (recycle gas to syngas feed gas) can be quite high in commercial practice, such as from 3:1 to 7:1, due to equilibrium limitations in methanol conversion. In the second stage, methanol is fed to a dimethyl ether reactor where dimethyl ether and water are produced. Water is separated from dimethyl ether in a subsequent stage.

Air separation (for providing an enriched oxygen feed), autothermal reforming, and substantial internal product recycle imposes significant operating and equipment costs for conventional systems for producing dimethyl ether from natural gas. It would therefore be desirable to provide new integrated processes for the production of dimethyl ether from natural gas.

A newer method has been developed for a one-stage process of converting syngas to dimethyl ether. The newer method uses two separate catalysts in a single reactor to convert CO and $H_2$ to methanol with a metal catalyst and the methanol to dimethyl ether with an acid second catalyst. However, the two catalyst being present together and mixed causes catalyst deactivation over time. For example, the acid catalysts produce coke that deactivates the metal catalysts. Further, the metal from the catalysts tends to migrate under reaction conditions preferentially to the acid sites of the acid catalysts and poison or deactivate the acid portion of the bifunctional catalyst.

SUMMARY

The present disclosure relates to bifunctional catalyst systems and methods of producing such bifunctional catalyst systems that include a carbon-coated acid catalyst and/or a carbon-coated metal catalyst. It is believed that the carbon coating acts as a barrier to reduce the migration of metal cations onto acidic sites, which would deactivate the catalyst system.

A method of the present disclosure may comprise: coating a metal catalyst particle with a carbon-containing small molecule to produce a coated metal catalyst particle; carbonizing the carbon-containing small molecule on the coated metal catalyst particle to produce a carbon-coated metal catalyst particle; and mixing the carbon-coated metal catalyst particle with an acid catalyst particle to produce an acid/metal bifunctional catalyst system.

Another method of the present disclosure may comprise: coating an acid catalyst particle with a carbon-containing small molecule to produce a coated acid catalyst particle; carbonizing the carbon-containing small molecule on the coated acid catalyst particle to produce a carbon-coated acid catalyst particle; and mixing the carbon-coated acid catalyst particle with a metal catalyst particle to produce an acid/metal bifunctional catalyst system.

An acid/metal bifunctional catalyst system of the present disclosure may be produced according to either or a combination of both the foregoing example methods.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present disclosure relates to bifunctional catalyst systems and methods of producing such bifunctional catalyst systems that include a carbon-coated acid catalyst and/or a carbon-coated metal catalyst. It is believed that the carbon coating acts as a barrier to reduce the migration of metal cations onto acidic sites, which would deactivate the catalyst system.

Acid/Metal Bifunctional Catalyst Systems

The acid/metal bifunctional catalyst systems of the present disclosure comprises an acid catalyst having a carbon coating (referred to herein as a carbon-coated acid catalyst) and/or a metal catalyst having a carbon coating (referred to herein as a carbon-coated metal catalyst). Without being limited by theory, it is believed that the carbon coating on either catalyst particle reduce catalyst deactivation. The catalyst deactivation was caused by the side products generated during the reactions of syngas to methanol and methanol to dimethyl ether. Such side products can include, but are not limited to, water, acidic acid, formic acid, and other oxygenates. The side products promote the formation and migration of metal cations (e.g., Cu cations) onto the acidic sites of the acid catalyst. Again, without being limited by theory, it is believed that the carbon coating acts as a barrier to reduce the migration of metal cations onto acidic sites, thus diminishing the catalyst deactivation.

Generally, the carbon-coated acid catalyst particles and/or carbon-coated metal catalyst particles are produced by coating the acid catalyst particles and/or metal catalyst particles with a carbon-containing small molecule and then carbonizing the carbon-containing small molecule.

As used herein, the terms "coat," "coating," and the like, do not imply any particular degree of coating on a particle. In particular, the terms "coat" or "coating" do not imply 100% coverage by the coating on a particle. Further, because the acid catalyst particles and/or metal catalyst particles may be porous, the compounds used in the coating may infiltrate portions of the porosity and, in effect, impregnate portions of the particles. The terms "coat," "coating," and the like encompass such mechanisms.

Figure 1:
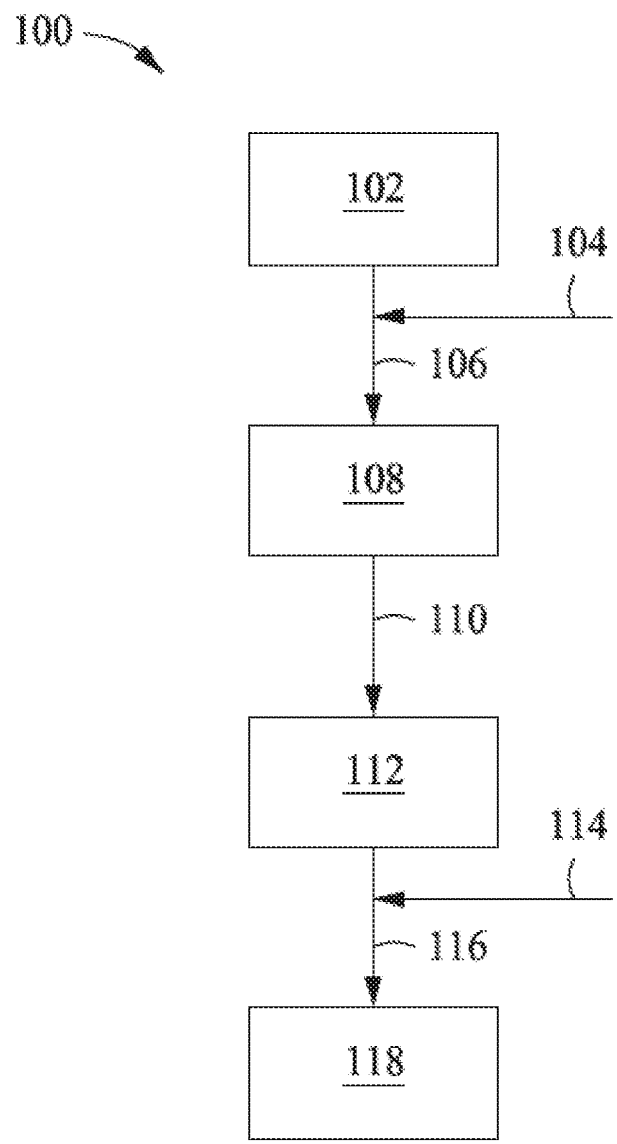
FIG. 1 is a flowchart illustrating an example method of preparing acid/metal bifunctional catalyst.

FIG. 1 is a flowchart illustrating an example method 100 of preparing acid/metal bifunctional catalyst system. The method includes coating 106 a catalyst particle 102 (acid catalyst particle or metal catalyst particle) with a carbon-containing small molecule 104 to produce a coated catalyst particle 108.

The acid catalyst may be any acid catalyst suitable for converting methanol to dimethyl ether. Generally, the acid property of the acid catalyst may be Lewis acidity, Bronsted acidity, or the combination of the both Lewis acidity and Bronsted acidity. Examples of acid catalysts can include, but are not limited to, a zeolite, an ion exchanged zeolite, molecular sieves (e.g., SAPO), metal oxides (e.g., oxides of aluminum, silicon, zirconium, boron, and combinations thereof like alumiosilicates, boroaluminosilicates, borosilicates, and the like), and any combination thereof. Examples of zeolites can include, but are not limited to, MCM-49, HZSM-5-5B, mordenite, ZSM-35, ZSM-48, ZSM-11, Chabazite, boric acid modified alumina, phosphorus oxide modified alumina, ERS-8, MoPOx, and the like, and any combination thereof. Examples of combinations of acid catalyst include, but are not limited to, $WO_3$, $ZrO_2$, $SiO_2$, resins, metal organic frameworks (MOFs), zeolite imidazolate frameworks (ZIFs), and the like, and any combination thereof.

The metal catalyst may be any metal catalyst suitable for converting CO and $H_2$ to methanol. Examples of metal catalysts can include, but are not limited to, a M1/M2/Al catalyst, wherein M1 is selected from the group consisting of Cu, Cr, Ag, Au, Ru, Rh, Pd, Re, Os, Ir, Pt, and any combination thereof, wherein M2 is selected from the group consisting of Ti, V, Cr, Mn, Fe, Co, Ni, Zn, a rare earth metal, a La series metal, a Y series metal, and any combination thereof, and wherein M1 and M2 are different.

The carbon-containing small molecule may be a molecule having a molecular weight of about 900 g/mol or less and contain at least 25 wt % (or 50 wt % or more) carbon. The carbon-containing small molecule should be a compound capable of producing carbon deposits on the metal catalyst and/or the acid catalyst during calcination in an inert atmosphere. Preferably, the carbon-containing small molecule comprises hydrogen, oxygen, and carbon in combination at 90 wt % or more of the carbon-containing small molecule. In the next step of carbonizing 110, it is preferably that only carbon residue remain, so carbon-containing small molecule that comprise elements like sodium are not preferred as the sodium would also remain in the coating.

Examples of carbon-containing small molecules can include, but are not limited to, organic oxygenates (e.g., alcohols of C1 to C10), an organic acid (e.g., pyruvic acid, levulinic acid, 2-ketogulonic acid, keto-gluconic acid, thioglycolic acid, 4-acetylbutyric acid, 1,3-acetonedicarboxylic acid, 3-oxo propanoic acid, 4-oxo butanoic acid, 2,3-diformyl succinic acid, 5-oxo pentanoic acid, 4-oxo pentanoic acid, ethyl glyoxylate, glycolic acid, glycine, glyoxylic acid, oxamic acid, glyoxylic acid 2-oxime, ethylenediaminetetraacetic acid, nitrilotriacetic acid, N-methylaminodiacetic acid, iminodiacetic acid, diglycolic acid, malic acid, gluconic acid, acetylacetone, citric acid), a saccharide (e.g., glucose), a polysaccharide, ethylene glycol, a polyethylene glycol, propylene glycol, a polypropylene glycol, and the like, and any combination thereof. Preferred organic acids are glyoxylic acid, oxalacetic acid, 2-ketogulonic acid, alpha-ketoglutaric acid, 2-ketobutyric acid, pyruvic acid, keto-gluconic acid, thioglycolic acid, glycolic acid, and combinations thereof. In any embodiment, the organic complexing agent can be glyoxylic acid, gluconic acid, oxalacetic acid, or a combination thereof. In any embodiment, the organic acid can comprise a —COOH functional group and at least one additional functional group selected from carboxylic acid: —COOH, hydroximate acid: —NOH—C=O, hydroxo: —OH, keto: —C=O, amine: —$NH_2$, amide: —C(=O)—$NH_2$, imine: —C=NOH, epoxy: =COC=, thiol: —SH, and any combination thereof. For example, the organic acid can be a bidentate ligand.

Coating 106 the catalyst particle 102 can be achieved by exposing the catalyst particle 102 to an aqueous suspension of the carbon-containing small molecule 104. Then, the mixture may be filtered or water evaporated optionally followed by drying. Drying may occur in an inert gas (e.g., nitrogen, argon, and the like, and any combination thereof) or oxygen-containing gas (e.g., oxygen, air, oxygen-enriched air, and the like) at temperature of about 75° C. to about 120° C. (or about 85° C. to about 110° C., or about 95° C. to about 105° C.) for a suitable amount of time (e.g., about 10 minutes to about 48 hours, or about 1 hour to about 24 hours, or about 8 hours to about 18 hours) to achieve a desired amount of dryness.

The amount of carbon-containing small molecule 104 used relative to the catalyst particles 102 may be based on the absorption capacity of the catalyst particles 102. The absorption capacity can be measured using distilled water at room temperature and ambient pressure per ASTM C128-15. The amount of carbon-containing small molecule 104 used for coating may be about 75% or greater (or about 75% to about 125%, or about 85% to about 110%, or about 90% to about 99%) of the absorption capacity of the catalyst particles 102.

After coating 106, method includes carbonizing 110 the coated catalyst particle 108 to yield a carbon-coated catalyst particle 112. Generally, carbonizing 110 is performed at conditions suitable for pyrolyitcally converting the carbon-containing small molecule coating to carbon. For example, carbonizing 110 can involve exposing the coated catalyst particle 108 to an elevated temperature of about 200° C. to about 400° C. (or about 250° C. to about 350° C.) in an inert atmosphere (e.g., nitrogen, carbon dioxide, argon, and the like, and any combination thereof) for about 10 minutes to about 24 hours (or about 1 hour to about 6 hours, or about 3 hours to about 12 hours, or about 8 hours to about 24 hours).

The method then includes mixing 116 the carbon-coated catalyst particle 112 with the other catalyst particle 114 to produce an acid/metal bifunctional catalyst system 118. That is, if the catalyst particle 102 is a metal catalyst particle, the other catalyst particle 114 is an acid catalyst particle, and vice versa. For example, the acid/metal bifunctional catalyst system 118 may comprise carbon-coated acid catalyst particles and metal catalyst particles that are not carbon coated. In another example, the acid/metal bifunctional catalyst system 118 may comprise carbon-coated metal catalyst particles and acid catalyst particles that are not carbon coated.

The other catalyst particle 114 optionally may be a carbon-coated catalyst particle produced by the method 100 or a similar method. For example, the acid/metal bifunctional catalyst system 118 may comprise carbon-coated acid catalyst particles and carbon-coated metal catalyst particles.

Optionally, additional catalyst particles of the same type may be included in the acid/metal bifunctional catalyst system 118 without carbon coating. For example, the acid/metal bifunctional catalyst system 118 may comprise carbon-coated acid catalyst particles, metal catalyst particles that are not carbon-coated, and acid catalyst particles that are not carbon-coated. Alternatively, the acid/metal bifunctional catalyst system 118 may comprise carbon-coated metal catalyst particles, metal catalyst particles that are not carbon-coated, and acid catalyst particles that are not carbon-coated. Alternatively, the acid/metal bifunctional catalyst system 118 may comprise carbon-coated acid catalyst particles, carbon-coated metal catalyst particles, metal catalyst particles that are not carbon-coated, and acid catalyst particles that are not carbon-coated. Alternatively, the acid/metal bifunctional catalyst system 118 may comprise carbon-coated acid catalyst particles, carbon-coated metal catalyst particles, and acid catalyst particles that are not carbon-coated. Alternatively, the acid/metal bifunctional catalyst system 118 may comprise carbon-coated acid catalyst particles, carbon-coated metal catalyst particles, and metal catalyst particles that are not carbon-coated.

Regarding the mixing 116, a carbon-coated catalyst particle 112 described herein can then be wet or dry mixed with the other catalyst particle 114 and optionally inert particles to produce an acid/metal bifunctional catalyst system 118 suitable for, among other things, converting syngas to dimethyl ether in a single reactor. Optionally, the mixture can further include binders and be extruded to form the acid/metal bifunctional catalyst system.

By way of nonlimiting example, an acid/metal bifunctional catalyst system 118 can be formed by dry admixing the carbon-coated catalyst particle 112 described herein, the other catalyst particle 114, and optionally inert particles.

In another nonlimiting example, an acid/metal bifunctional catalyst system can be formed by mixing the carbon-coated catalyst particle 112 described herein with the other catalyst particle 114 and a binder to form a dough; and extruding the dough to produce the acid/metal bifunctional catalyst system 118. Said acid/metal bifunctional catalyst system 118 can be used as extruded or optionally dried (e.g., at about 25° C. to about 90° C. for about 5 minutes to about 24 hours), calcined (e.g., as described above), ground, or any combination thereof. Examples of binders include, but are not limited to, clay, theta-alumina, delta-alumina, alpha-alumina, silica, titania, zirconia, boric acid, carbon, organic compounds (e.g., polymers), and the like, and any combination thereof).

In another nonlimiting example, an acid/metal bifunctional catalyst system 118 can be formed by mixing the carbon-coated catalyst particle 112 described herein with the other catalyst particle 114 and a solvent to form a slurry; heating the slurry; and drying the slurry to produce the acid/metal bifunctional catalyst system 118. Said acid/metal bifunctional catalyst system 118 can be used as extruded or optionally dried (e.g., at about 25° C. to about 90° C. for about 5 minutes to about 24 hours), calcined (e.g., as described above), ground, or any combination thereof. Examples of solvents include, but are not limited to, water, methanol, ethanol, alcohols of $C_1$ to $C_{10}$, oxygenates, and the like, and any combination thereof.

The carbon-coated catalyst particle 118 (whether acid, metal, or both in combination) may be present in the acid/metal bifunctional catalyst system 118 at about 10 wt % to 100 wt % (or at about 10 wt % to at about 90 wt %, or at about 10 wt % to at about 25 wt %, or at about 15 wt % to at about 40 wt %, or at about 25 wt % to at about 75 wt %, or at about 50 wt % to at about 75 wt %, or at about 65 wt % to at about 90 wt %, or at about 80 wt % to at 100 wt %) relative to a total catalyst weight in the acid/metal bifunctional catalyst system 118.

Optionally, the acid/metal bifunctional catalyst system 118 may further comprise inert particles up to about 50 wt % (or about 1 wt % to about 50 wt %, or about 5 wt % to about 25 wt %, or about 20 wt % to about 50 wt %) based on a total weight of the acid/metal bifunctional catalyst system 118.

The acidity of the acid/metal bifunctional catalyst system 118 measured with pyridine for Bronsted acid cites (1545 $cm^{-1}$ and 1450 $cm^{-1}$ infrared spectra bands) and ammonia for Lewis acid cites (1620 $cm^{-1}$ and 1450 $cm^{-1}$ infrared spectra bands) may be cumulatively about 1 site to about 250 sites, or 25 sites to 200 site, or 50 sites to 150 sites.

Direct Synthesis of Dimethyl Ether from Syngas

Figure 2:
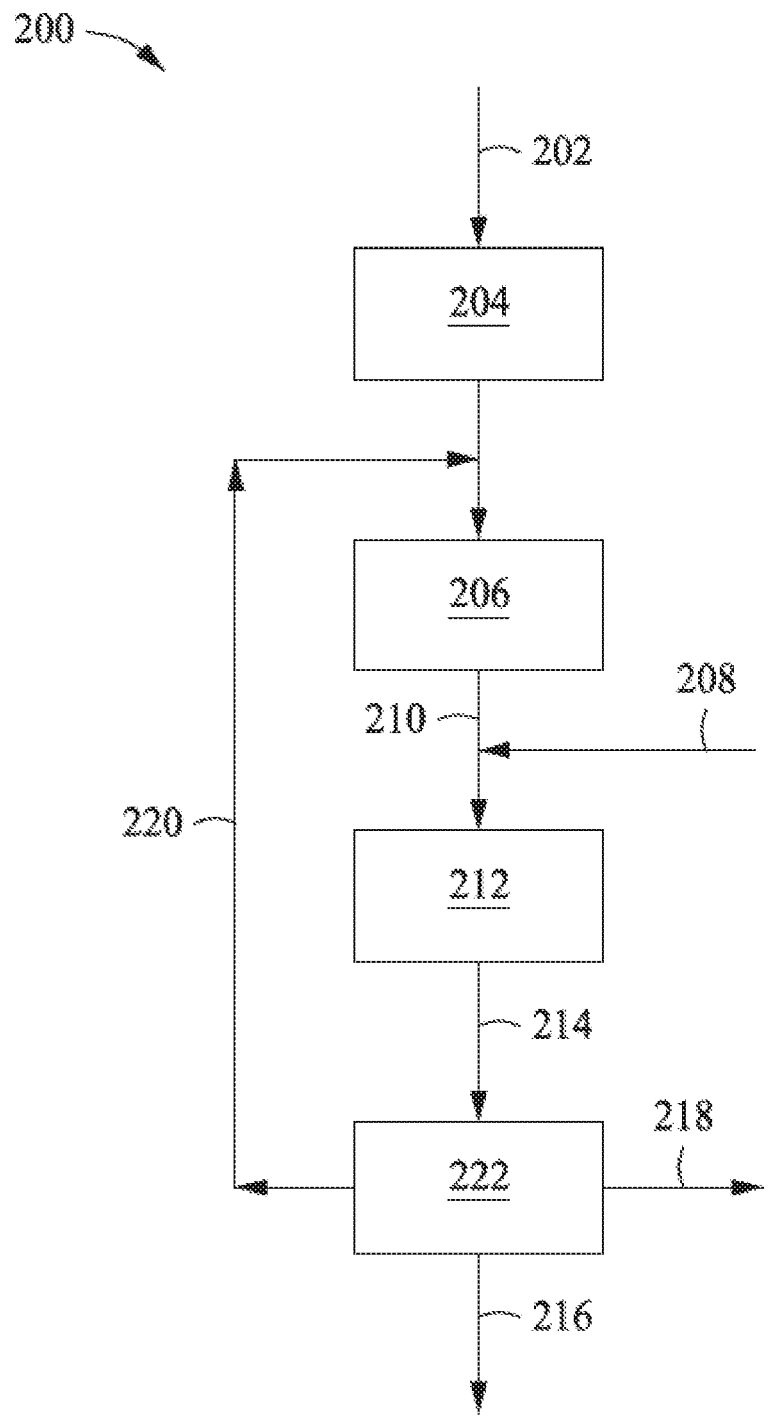
FIG. 2 is a flowchart illustrating an example integrated system and process for producing dimethyl ether from natural gas according to one or more embodiments of the present invention.

An example 200 method and system for the production of dimethyl ether from natural gas is illustrated in FIG. 2. A natural gas stream 202 is fed to a pretreater 204 to remove contaminants such as sulfur, chlorides and olefins. The pretreater 204 may be a single unit or, more likely, it is a series of units for removing the different types of contaminants found in the natural gas stream 204. For example, the pretreater 204 may include a desulfurizing column for removing sulfur. The pretreater 204 can also include a guard bed to remove chlorides and/or a hydrotreater to covert olefins to paraffins.

The pretreated natural gas may then be fed to a reformer 206, which may be a reverse flow reactor, to convert the natural gas to a syngas 210. A recycled $CO_2$ stream 220, which may also include recycled methane, can be fed with the treated natural gas to the reformer 206. It is noted that the pretreated natural gas stream may contain essentially zero $CO_2$ (such as the gas in pipeline gas) or it may have a high $CO_2$ content. Steam may also be added to the reformer 206 to promote the conversion of natural gas to syngas.

Steam 208 and syngas 210 are co-fed to a dimethyl ether reactor 212 to produce a product stream 214, which can include dimethyl ether, carbon dioxide, methane, hydrogen, and other byproducts. The dimethyl ether reactor 212 may operate a temperature of about 200° C. to about 300° C. (or about 230° C. to about 270° C.), a pressure of about 20 bar to about 50 bar (or about 30 bar to about 40 bar), and a gas hourly space velocity (GHSV) of about 1,000 $hr^{-1}$ to about 8,000 $hr^{-1}$ (or about 1,500 $hr^{-1}$ to about 3,000 $hr^{-1}$).

The product stream 214 may be fed to one or more separators 222 to separate the methane, carbon dioxide, and other byproducts 218 from dimethyl ether 216. Methane and carbon dioxide may be recycled back to the reformer 206 via the recycle stream 28. The separation of the products may be accomplished using various separation processes including refrigeration, distillation/fractionation, high-pressure or low-pressure flash separation, or membrane separation.

Prior to running the foregoing method, the acid/metal bifunctional catalyst system may be activated by exposure to hydrogen at elevated temperatures (e.g., about 150° C. to about 350° C., or about 200° C. to about 300° C.).

Direct dimethyl ether synthesis may be performed by converting syngas to methanol (Eq. 1) with the in-situ dehydration of methanol to dimethyl ether (Eq. 3). Advantageously, both reactions can occur in the same reactor such that the methanol is nearly instantaneously dehydrated to dimethyl ether as it is produced. In addition, a water gas shift reaction (Eq. 2) is typically present.

$$CO+2H_2 \leftrightarrow CH_3OH \ \Delta H_r=-90.84 \text{ kJ/mole} \quad \text{(Eq. 1)}$$

$$CO+H_2O \leftrightarrow CO_2+H_2 \ \Delta H_r=-41.27 \text{ kJ/mole} \quad \text{(Eq. 2)}$$

The equilibrium of the methanol reaction (Eq. 1) at high temperatures required to promote kinetics, is reactant favored and limits the overall syngas conversion in a traditional methanol process. However, the disclosed acid/metal bifunctional catalyst system may enable the in-situ dehydration of methanol immediately after it is formed, which maintains the system sufficiently far from equilibrium limitations of Eq. 1 and may improve the per-pass conversion of syngas.

Various by-products can also be produced during the conversion of syngas to methanol (e.g., methane, water, carbon dioxide, formic acid) and the conversion of methanol to dimethyl ether (e.g., acetates, hydrocarbons, methane, water, and coke). Acetates are known to facilitate metal sintering and metal ion-exchange on the acid catalyst that lead to catalyst deactivation.

Because the addition of steam reduces the per-pass selectivity to dimethyl ether by converting some carbon monoxide to carbon dioxide (Eq. 2), the amount of water present in the dimethyl ether reactor would conventionally be limited to the minimal amounts desired to mitigate coke formation. However, it has been found that the addition of steam in the proposed integrated process can be used to control production of $CO_2$ in the dimethyl ether reactor, which can improve the carbon efficiency of the system or process as described in further detail herein. Furthermore, surprisingly, it has been found that co-feeding steam in such quantities can reduce the selectivity towards hydrocarbons and oxygenates, thereby improving the acid/metal bifunctional catalyst system stability.

The total reaction of a system for the synthesis of dimethyl ether (Eq. 4) including the water-gas-shift reaction, methanol synthesis reaction, and dehydration reaction is exothermic.

$$2CH_3OH \leftrightarrow CH_3-O-CH_3+H_2O \ \Delta H_r=-21.26 \text{ kJ/mole} \quad \text{(Eq. 3)}$$

$$3CO+3H_2 \leftrightarrow CH_3-O-CH_3+CO_2 \ \Delta H_r=-246 \text{ kJ/mole} \quad \text{(Eq. 4)}$$

It has been found that carbon efficiency can be improved by controlling feed parameters, particularly the amount of water added to either the reforming reactor or the dimethyl ether reactor. Conventionally, syngas conversion process use factors like $H_2$:CO ratio or M-value, which is $(H_2-CO_2)/(CO+CO_2)$, to define the ideal feed to the syngas conversion reactor. The numerical value selected for this metric typically reflects the ideal stoichiometry for the desired product reaction. Additionally, the presence of water is typically ignored or treated like an inert.

Water, however, plays a critical role in the integrated process described herein. Water may be added in amount to leverage the water-gas-shift reaction to co-produce $CO_2$ (as needed to maximize carbon efficiency) in the dimethyl ether reactor. The amount of water added, is a function of the syngas composition (namely the amount of $CO/CO_2/H_2/H_2O$ present in the feed to the dimethyl ether reactor), which is a function of the steam reforming relative to the dry reforming carried out in the syngas reactor.

A preferred feed to the dimethyl ether reactor may be described with a modified M-value (Mm) per the following equation.

$$Mm = \frac{H_2 - CO_2 + H_2O}{CO + CO_2 - H_2O}$$

Water may be added to the process in total, either in the syngas reactor for steam reforming or in the dimethyl ether reactor. Independent of how the water is split between the reactors this corresponds to a modified M-value of about 1.4 to 1.8 (or 1.5 to 1.7, or 1.6).

Various reforming processes may be employed to produce syngas from such a natural gas feedstream including, but not limited to, partial oxidation, steam methane reforming, autothermal reforming, dry reforming, and the like, and any combination thereof. Preferably, the natural gas stream is reformed using a reverse flow reactor.

Any natural gas feedstream can be reformed into syngas. As used herein, "natural gas" refers to a hydrocarbon feed that is predominantly $C_1$ to $C_4$ hydrocarbons, and it may be predominantly methane. The natural gas feedstream can also include carbon dioxide. For simplicity, examples used herein may make specific reference to methane; however, it should be understood that natural gas feed streams further comprising $C_2$-$C_4$ hydrocarbons may also be used. General equations for the dry reforming and steam reforming for such hydrocarbons are shown in Eq. 5 and Eq. 6, respectively.

$$C_nH_{2n+1}+CO_2 \rightarrow 2nCO+(n+1)H_2 \quad \text{(Eq. 5)}$$

$$C_nH_{2n+1}+H_2O \rightarrow nCO+(2n+1)H_2 \quad \text{(Eq. 6)}$$

In order to improve carbon efficiency of the system, it is desirable to provide a feed of natural gas and carbon dioxide to the reverse flow reactor at a natural gas:carbon dioxide molar ratio of about 1:1, such as about 0.8:1 to about 1.1:1. For example, 2 moles of $CO_2$ and 2 moles of methane may produce 4 moles of CO and 4 moles of $H_2$ as shown in Eq. 7.

$$2CO_2+2CH_4 \leftrightarrow 4CO+4H_2 \quad \text{(Eq. 7)}$$

If the products of Eq. 5 were then fed to the dimethyl ether reactor with steam as a co-feed, the following products would be produced: 1 mole of dimethyl ether, 2 moles of $CO_2$ and 1 mole of $H_2$ (Eqs. 4 and 2).

The reverse flow reactor for reforming the natural gas to syngas may operate at a temperature of about 300° C. and about 1400° C. (or about 500° C. and about 1000° C.) and a pressure range of about 1 bar and about 100 bar (or about 10 bar to about 50 bar).

The effluent from the dimethyl ether reactor may be separated into dimethyl ether, $CO_2$ (optionally with any unreacted $CH_4$, CO, and/or $H_2$), and other byproducts. Any one or combination of separation processes may be employed to perform such separations including, but not limited to, refrigeration, distillation/fractionation, flash separation and membrane separation. The $CO_2$, $CH_4$, and any unreacted intermediates may be recycled as described herein.

Advantageously, recycle streams having desirable compositions can be obtained from separation processes downstream of the dimethyl ether reactor. These recycle streams can be used to improve the carbon efficiency of the integrated system and/or can provide other advantages.

In any embodiment, $CO_2$ and $CH_4$, and optionally CO, recovered downstream of dimethyl ether reactor may be recycled upstream of the syngas generation reactor. The $CO_2$ may be provided in sufficient quantities such that when added to the $CO_2$ native to the natural gas feed will achieve the desired natural gas:carbon dioxide ratio, such as a methane:carbon dioxide molar ratio of about 1:1, such as about 0.9:1.1 to about 1.1:0.9. In some cases, it may be desirable to recycle at least a portion of the $CO_2$ and $CH_4$, and optionally CO and methanol, upstream of the dimethyl ether reactor but downstream of the syngas generator reactor.

Hydrogen may also be recovered from the separation processes and used as fuel. Optionally, at least a portion of the hydrogen can be recycled upstream of the dimethyl ether reactor.

Example Embodiments

A first nonlimiting example embodiment is a method comprising: coating a metal catalyst particle with a carbon-containing small molecule to produce a coated metal catalyst particle; carbonizing the carbon-containing small molecule on the coated metal catalyst particle to produce a carbon-coated metal catalyst particle; and mixing the carbon-coated metal catalyst particle with an acid catalyst particle to produce an acid/metal bifunctional catalyst system.

A second nonlimiting example embodiment is a method comprising: coating an acid catalyst particle with a carbon-containing small molecule to produce a coated acid catalyst particle; carbonizing the carbon-containing small molecule on the coated acid catalyst particle to produce a carbon-coated acid catalyst particle; and mixing the carbon-coated acid catalyst particle with a metal catalyst particle to produce an acid/metal bifunctional catalyst system.

The two foregoing example embodiments may further comprise one or more of the following: Element 1: wherein the acid catalyst particle is a carbon-coated acid catalyst particle for the first nonlimiting example embodiment or wherein the metal catalyst particle is a carbon-coated metal catalyst particle for the second nonlimiting example embodiment; Element 2: wherein carbonizing comprises: exposing the coated metal catalyst particle (or the coated acid catalyst particle) to an elevated temperature of 200° C. to 400° C. in an inert atmosphere for 10 minutes to 24 hours; Element 3: wherein coating comprises: exposing the metal catalyst particle (or the acid catalyst particle) to an aqueous suspension of the carbon-containing small molecule; Element 4: wherein an amount of the carbon-containing small molecule used for the coating step is 75% or greater of an absorption capacity of the metal catalyst particle (or the acid catalyst particle); Element 5: wherein the carbon-containing small molecule is selected from the group consisting of: a saccharide, a polysaccharide, ethylene glycol, a polyethylene glycol, propylene glycol, a polypropylene glycol and any combination thereof; Element 6: wherein the acid catalyst particle is selected from the group consisting of a zeolite, an ion exchanged zeolite, a molecular sieve, a metal oxide, and any combination thereof; Element 7: wherein the metal catalyst particle is a M1/M2/Al catalyst, wherein M1 is selected from the group consisting of Cu, Ag, Au, Ru, Rh, Pd, Re, Os, Ir, Pt, and any combination thereof, and wherein M2 is selected from the group consisting of Ti, V, Cr, Mn, Fe, Co, Ni, Zn, a rare earth metal, a La series metal, a Y series metal, and any combination thereof; Element 8: wherein the acid catalyst particle (or the metal catalyst particle) is present at 10 wt % to 90 wt % relative to a total catalyst weight in the acid/metal bifunctional catalyst system; Element 9: wherein the acid catalyst particle (or the metal catalyst particle) is present at 25 wt % to 75 wt % relative to a total catalyst weight in the acid/metal bifunctional catalyst system; Element 10: wherein the acid/metal bifunctional catalyst system further comprises inert particles up to 50 wt % of a total weight of the acid/metal bifunctional catalyst system; Element 11: wherein the mixing step comprises: dry mixing the carbon-coated metal catalyst particle (or the carbon-coated acid catalyst particle) with the acid catalyst (or the metal catalyst particle) to produce the acid/metal bifunctional catalyst system; Element 12: wherein the mixing step comprises: mixing the carbon-coated metal catalyst particle (or the carbon-coated acid catalyst particle) with the acid catalyst (or the metal catalyst particle) and a binder to form a dough; and extruding the dough to produce the acid/metal bifunctional catalyst system; Element 13: wherein the mixing step comprises: mixing the carbon-coated metal catalyst particle (or the carbon-coated acid catalyst particle) with the acid catalyst (or the metal catalyst particle) and a solvent to form a slurry; heating the slurry; and drying the slurry to produce the acid/metal bifunctional catalyst system; and Element 14: activating the acid/metal bifunctional catalyst system of any preceding claim in hydrogen at 150° C. to 350° C.; and reacting the activated acid/metal bifunctional catalyst system with a feedstream comprising hydrogen and carbon monoxide. Examples of combinations include, but are not limited to, two or more of Elements 1-5 in combination; Elements 6 and 7 in combination; Element 10 in combination with one of Elements 9 or 10; two or more of Elements 1-10 in combination; one of Elements 11-13 in combination with any of the foregoing; one of Elements 11-13 in combination with one or more of Elements 1-10; and Element 14 in combination with any of the foregoing.

Additional nonlimiting example embodiments are an acid/metal bifunctional catalyst system produced according to the first nonlimiting example embodiment or the second nonlimiting example embodiment, either optionally further including or characterized by one or more of Elements 1-14.

Further, the first and second nonlimiting example embodiments may be combined to provide a method of producing each of the carbon-coated metal catalyst particle and the carbon-coated acid catalyst particle, which can then be mixed to form the acid/metal bifunctional catalyst system that comprises the carbon-coated metal catalyst particle and the carbon-coated acid catalyst particle.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

To facilitate a better understanding of the embodiments of the present invention, the following examples of preferred or representative embodiments are given. In no way should the following examples be read to limit, or to define, the scope of the invention.

EXAMPLES

Preparation of Carbon Coated CuZnAl (Sample 1)

The solution absorption capacity of 125 μm to 160 μm CuZnAl powders (available from Clariant) estimated with distilled water was 0.95 mL/g. The precursor compound used for carbon deposition was 24.3 wt % gluconic acid aqueous solution. The volume of impregnation solution was 95% of the absorption capacity of CuZnAl powders. As an example of sample preparation, 18.05 mL of 24.3 wt % gluconic acid solution was used to impregnate 20.00 g of CuZnAl powders. After impregnation, the gluconic acid impregnated CuZnAl powders were dried in air at 120° C. for 16 hrs. Then, the sample was placed in a box furnace, and the furnace was purged with nitrogen flow for 1 hr to reduce residual oxygen concentration inside the furnace. The furnace was ramped from room temperature to 300° C. at rate of 10° F./min (5.6° C./min) in nitrogen. The nitrogen flowing rate is set at 5 volume/volume catalyst/minute. The samples were held at 300° C. in nitrogen for 3 hrs.

Preparation of Carbon Coated CuZnAl (Sample 2)

The solution absorption capacity of 125 μm to 160 μm CuZnAl powders estimated with distilled water was 0.95 mL/g. The precursor compound used for carbon deposition was 24.3 wt % gluconic acid aqueous solution. The volume of impregnation solution was 95% of the absorption capacity of CuZnAl powders. As an example of sample preparation, 18.05 mL of 24.3 wt % gluconic acid solution was used to impregnate 20.00 g of CuZnAl powders. After impregnation, the gluconic acid impregnated CuZnAl powders were dried in air at 120° C. for 16 hrs. Then, the sample was placed in a box furnace, and the furnace was purged with nitrogen flow for 1 hr to reduce residual oxygen concentration inside the furnace. The furnace was ramped from room temperature to 538° C. (1000° F.) at rate of 10° F./min (5.6° C./min) in nitrogen. The nitrogen flowing rate is set at 5 volume/volume catalyst/minute. The samples were held at 538° C. in nitrogen for 3 hrs.

Preparation of Carbon Coated ZMS-5/$Al_2O_3$ (Sample 3)

The solution absorption capacity of 125 μm to 160 μm ZMS-5 powders estimated with distilled water was 1.0 mL/g. The precursor compound used for carbon deposition was 24.3 wt % gluconic acid aqueous solution. The volume of impregnation solution was 95% of the absorption capacity of ZSM-5 powders. As an example of sample preparation, 9.5 mL of 24.3 wt % gluconic acid solution was used to impregnate 10.00 g of ZSM-5 powders. After impregnation, the gluconic acid impregnated ZSM-5 powders were dried in air at 120° C. for 16 hrs. Then, the sample was placed in a box furnace, and the furnace was purged with nitrogen flow for 1 hr to reduce residual oxygen concentration inside the furnace. The furnace was ramped from room temperature to 538° C. at rate of 10° F./min (5.6° C./min) in nitrogen. The nitrogen flowing rate is set at 5 volume/volume catalyst/minute. The samples were held at 538° C. in nitrogen for 3 hrs.

Catalysts Properties

Acid/metal bifunctional catalyst systems were prepared as 50 wt % to 50 wt % mixtures of an acid catalyst and a metal catalyst according to Table 1. The catalyst particles were simply dry mixed in these examples.

TABLE 1

|  | CuZnAl | Sample 1 | Sample 2 | ZSM-5 | Sample 3 |
| --- | --- | --- | --- | --- | --- |
| Catalyst 1 (reference) | 50 wt % |  |  | 50 wt % |  |
| Catalyst 2 |  | 50 wt % |  | 50 wt % |  |
| Catalyst 3 |  |  | 50 wt % |  | 50 wt % |
| Catalyst 4 | 50 wt % |  |  |  | 50 wt % |

Catalyst Testing

In separate reactions, a reactor was charged with catalyst samples according to Catalysts 1-4 in Table 1 with 125 μm to 160 μm α-$Al_2O_3$ particles above and below the catalysts bed. The catalysts in the reactor were activated by flowing hydrogen at 250° C. over the catalyst bed for 120 minutes. Then, the catalyst were used in a syngas to dimethyl ether reaction under the following conditions: a temperature of 230° C. to 270° C., a pressure of 25 bar to 50 bar, and a gas hourly space velocity (GHSV) of 1,000 $hr^{-1}$ to 8,000 $hr^{-1}$. The reaction feed was 37 vol % to 50 vol % $H_2$, 40 vol % to 50 vol % CO, 13 vol % to 40 vol % $CO_2$, 0 vol % to 3 vol % $CH_4$, 5 vol % to 10 vol % Ar (used as an internal standard), and 0 vol % to 10 vol % of $H_2O$. A gas chromatograph fitted with a flame-ionization detector (FID), a thermal conductivity detector (TCD), and optionally a helium ionization detector (HID) (for low water concentrations of 20 ppm to 2 vol %) was used to analyze the product stream.

Figure 3:
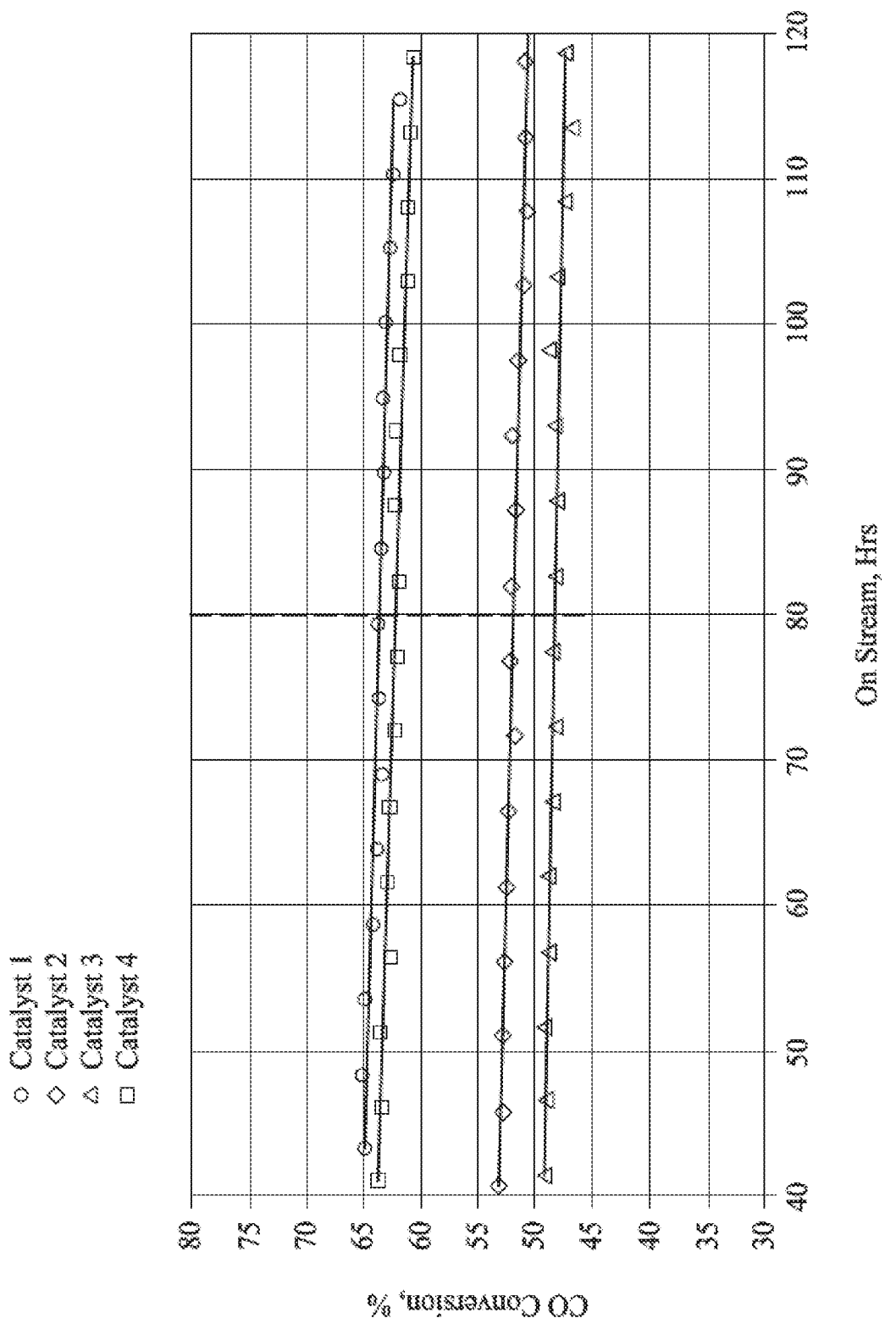
FIG. 3 is a plot of CO conversion activities for each of the Catalysts 1-4 over time from about 40 hours to about 120 hours of exposure to the reaction conditions.

FIG. 3 is a plot of CO conversion activities over time from about 40 hours to about 120 hours of exposure to the reaction conditions. Before 40 hrs on stream, the performances of all catalysts did not reach a stabilized state.

At 250° C., 35 bar pressure, and GHSV of 2100 $hr^{-1}$, the CO conversion activity of the reference catalyst system of Catalyst 1 at 80 hours on stream is around 63%. The deactivation of the reference catalyst system, Catalyst 1, follows the trend line with the equation of Y=−0.0393X+66.696. Accordingly, the CO conversion deactivates at the rate of −0.0393% per hr.

The CO conversion activity of Catalyst 2 at 80 hours on stream is around 52%. The carbon coating on the CuZnAl metal catalyst of Catalyst 2 reduces the CO conversion activity. It is possible that the metal catalyst surface was covered by carbon layers, which partially block metal function sites for CO conversion. The deactivation of Catalyst 2 follows the trend line with the equation of Y=−0.0326X+54.509. The CO conversion deactivates at the rate of −0.0326% per hr, which is slower than that of the reference Catalyst 1 of −0.0393% per hr. The carbon coating on CuZnAl calcined at 300° C. in nitrogen somewhat reduces the rate of the catalyst deactivation for CO conversion.

The CO conversion activity of Catalyst 3 at 80 hours on stream is around 48%. The carbon coating on CuZnAl metal catalyst of Catalyst 3 reduces the CO conversion activity more compared to the Catalyst 2. The higher temperature (538° C.) calcination produced denser C coating on CuZnAl, which made catalyst less accessible compared to Sample 1 (Catalyst 2), where the calcination was carried out at 300° C. in nitrogen. The deactivation of Catalyst 2 follows the trend line with equation of Y=−0.0242X+50.151. The CO conversion deactivates at the rate of −0.0242% per hr, which is much slower than the Catalyst 2. The carbon coating on CuZnAl calcined at 538° C. in nitrogen significantly reduces the rate of the catalyst deactivation for CO conversion.

The CO conversion activity of the Catalyst 4 at 80 hours on stream is around 62%, which is very close to that of the reference Catalyst 1. The carbon coating on ZSM-5 of Catalyst 4 did not reduce the CO conversion activity. CuZnAl is mostly responsible for CO conversion, which was not covered by carbon coating. The deactivation of the Catalyst 4 follows the trend line with the equation of Y=−0.0379X+65.219. The CO conversion deactivates at the rate of −0.0379% per hr, which is still slower than the reference Catalyst 1 with deactivation rate of −0.0393% per hr.

Figure 4:
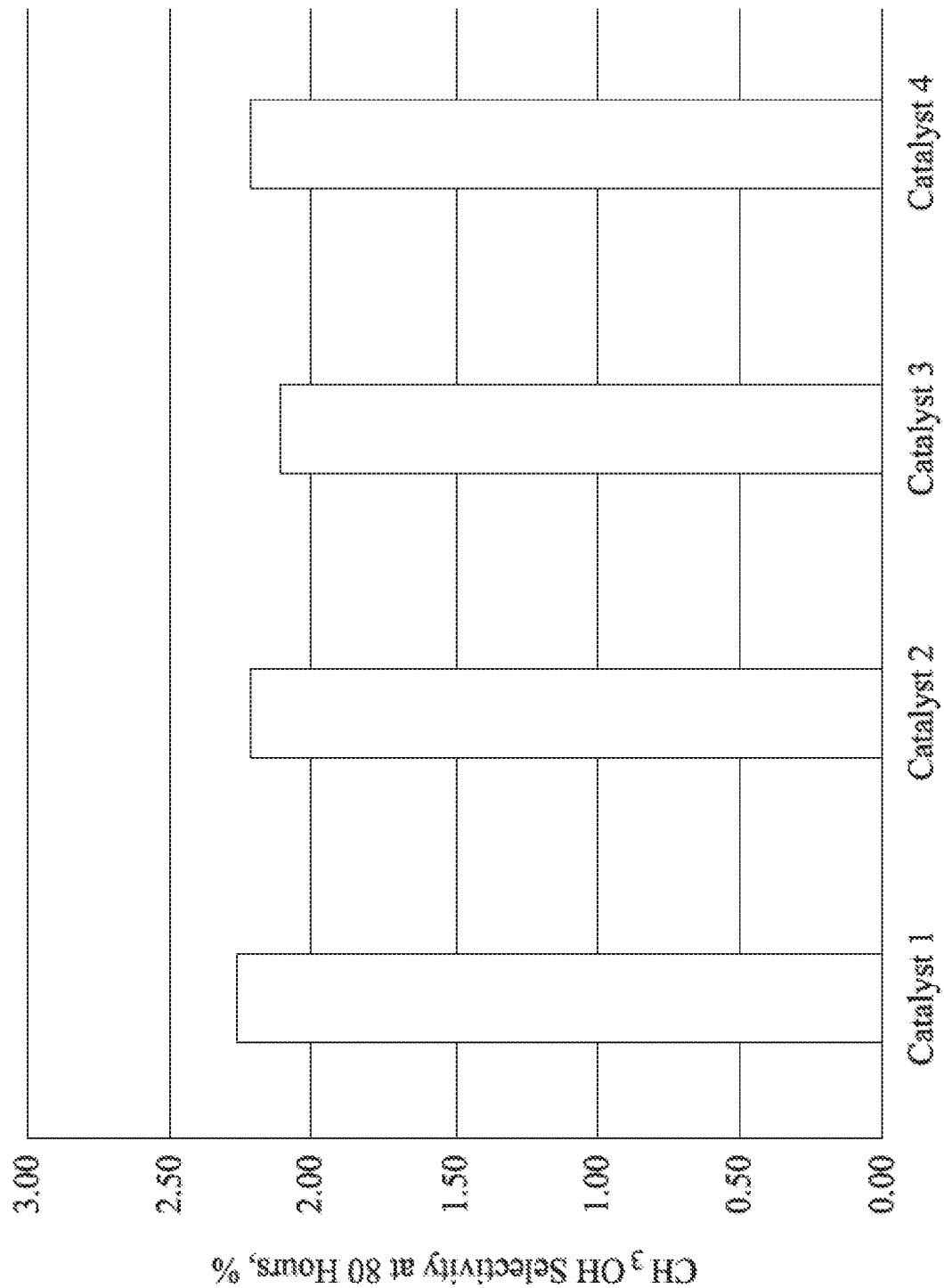
FIG. 4 is a plot of methanol selectivity for each of the Catalysts 1-4 after 80 hours on stream.

FIG. 4 is a plot of methanol selectivity for each of the Catalysts 1-4 after 80 hours on stream. Each of the Catalysts 1-4 have similar methanol selectivity. That is, the carbon coating applied does not appear to effect the methanol selectivity to a significant degree.

Figure 5:
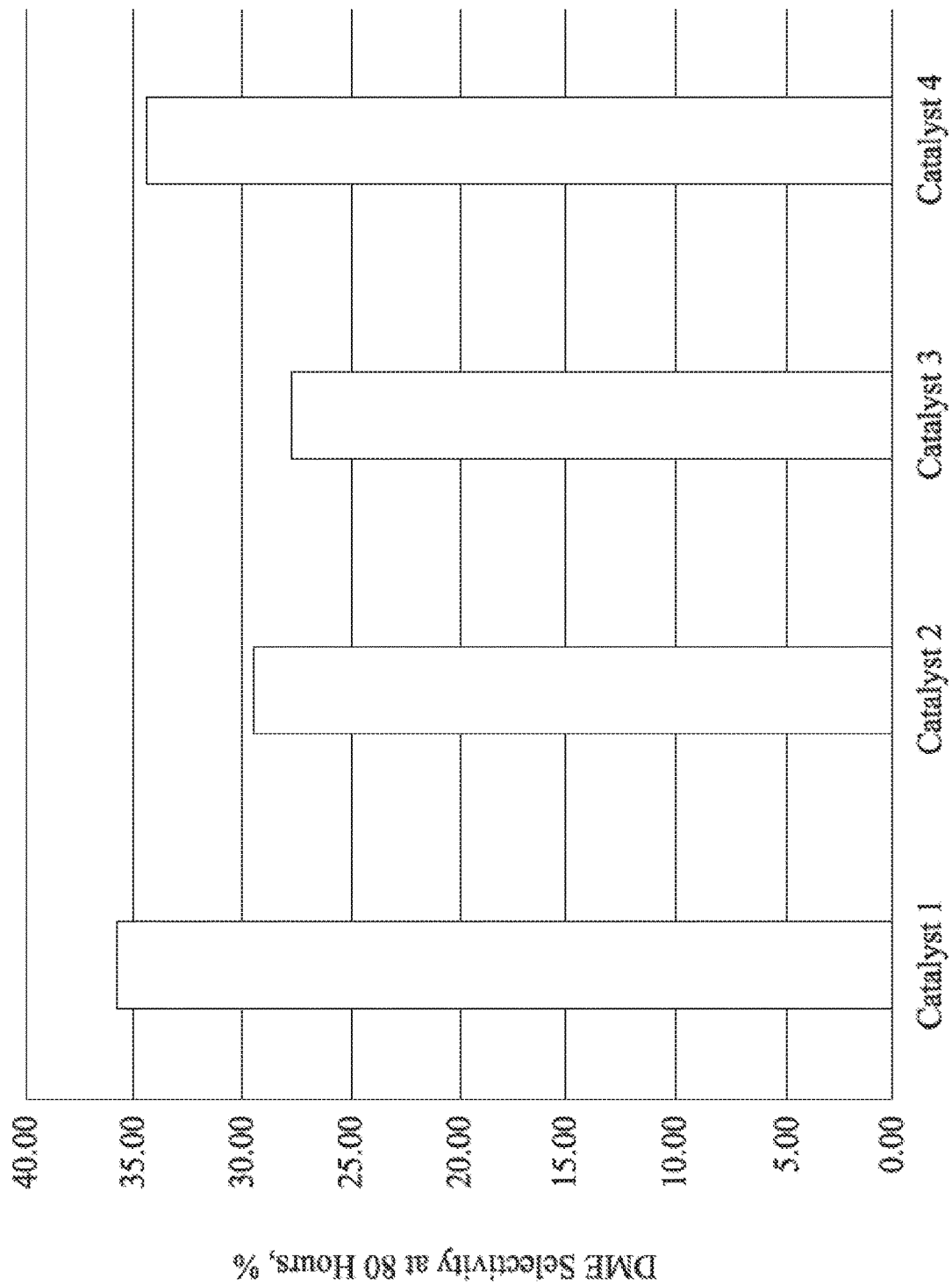
FIG. 5 is a plot of dimethyl ether selectivity for each of the Catalysts 1-4 after 80 hours on stream.

FIG. 5 is a plot of dimethyl ether (DME) selectivity for each of the Catalysts 1-4 after 80 hours on stream. The dimethyl ether selectivity is reduced slightly in Catalysts 2-4 as compared to reference Catalyst 1. The least reduction in dimethyl ether selectivity is in Catalyst 4 where the acid catalyst is carbon coated and the metal catalyst is not.

These examples illustrate that carbon coating of one or both of the acid and metal catalysts of the bifunctional catalyst systems described herein reduces the rate of deactivation of the catalyst with little to no effect on the methanol and dimethyl ether selectivities.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method comprising:
coating a metal catalyst particle with a carbon-containing small molecule to produce a coated metal catalyst particle;
carbonizing the carbon-containing small molecule on the coated metal catalyst particle to produce a carbon-coated metal catalyst particle; and
mixing the carbon-coated metal catalyst particle with an acid catalyst particle to produce an acid/metal bifunctional catalyst system.

2. The method claim 1, wherein the acid catalyst particle is a carbon-coated acid catalyst particle.

3. The method of claim 1, wherein carbonizing comprises: exposing the coated metal catalyst particle to an elevated temperature of 200° C. to 400° C. in an inert atmosphere for 10 minutes to 24 hours.

4. The method claim 1, wherein coating comprises: exposing the metal catalyst particle to an aqueous suspension of the carbon-containing small molecule.

5. The method of claim 1, wherein an amount of the carbon-containing small molecule used for the coating step is 75% or greater of an absorption capacity of the metal catalyst particle.

6. The method of claim 1, wherein the carbon-containing small molecule is selected from the group consisting of: a saccharide, a polysaccharide, ethylene glycol, a polyethylene glycol, propylene glycol, a polypropylene glycol and any combination thereof.

7. The method of claim 1, wherein the acid catalyst particle is selected from the group consisting of a zeolite, an ion exchanged zeolite, a molecular sieve, a metal oxide, and any combination thereof.

8. The method of claim 1, wherein the metal catalyst particle is a M1/M2/Al catalyst, wherein M1 is selected from the group consisting of Cu, Ag, Au, Ru, Rh, Pd, Re, Os, Ir, Pt, and any combination thereof, and wherein M2 is selected from the group consisting of Ti, V, Cr, Mn, Fe, Co, Ni, Zn, a rare earth metal, a La series metal, a Y series metal, and any combination thereof.

9. The method of claim 1, wherein the acid catalyst particle is present at 10 wt % to 90 wt % relative to a total catalyst weight in the acid/metal bifunctional catalyst system.

10. The method of claim 1, wherein the acid catalyst particle is present at 25 wt % to 75 wt % relative to a total catalyst weight in the acid/metal bifunctional catalyst system.

11. The method of claim 1, wherein the acid/metal bifunctional catalyst system further comprises inert particles up to 50 wt % of a total weight of the acid/metal bifunctional catalyst system.

12. The method of claim 1 wherein the mixing comprises: dry mixing the carbon-coated metal catalyst particle with the acid catalyst particle to produce the acid/metal bifunctional catalyst system.

13. The method of claim 1 wherein the mixing comprises: mixing the carbon-coated metal catalyst particle with the acid catalyst particle and a binder to form a dough; and extruding the dough to produce the acid/metal bifunctional catalyst system.

14. The method of claim 1 wherein the mixing comprises:
mixing the carbon-coated metal catalyst particle with the acid catalyst particle and a solvent to form a slurry;
heating the slurry; and
drying the slurry to produce the acid/metal bifunctional catalyst system.

15. The method of claim 1, further comprising:
activating the acid/metal bifunctional catalyst system in hydrogen at 150° C. to 350° C.; and
reacting the activated acid/metal bifunctional catalyst system with a feedstream comprising hydrogen and carbon monoxide.

16. A method comprising:
coating an acid catalyst particle with a carbon-containing small molecule to produce a coated acid catalyst particle;
carbonizing the carbon-containing small molecule on the coated acid catalyst particle to produce a carbon-coated acid catalyst particle; and
mixing the carbon-coated acid catalyst particle with a metal catalyst particle to produce an acid/metal bifunctional catalyst system.

17. The method claim 16, wherein the metal catalyst particle is a carbon-coated metal catalyst particle.

18. The method of claim 16, wherein carbonizing comprises:
exposing the coated acid catalyst particle to an elevated temperature of 200° C. to 400° C. in an inert atmosphere for 10 minutes to 24 hours.

19. The method of claim 16, wherein coating comprises:
exposing the acid catalyst particle to an aqueous suspension of the carbon-containing small molecule.

20. The method of claim 16, wherein the carbon-containing small molecule is selected from the group consisting of:
a saccharide, a polysaccharide, ethylene glycol, a polyethylene glycol, propylene glycol, a polypropylene glycol and any combination thereof.

21. The method of claim 16, wherein the acid catalyst particle is selected from the group consisting of a zeolite, an ion exchanged zeolite, a molecular sieve, a metal oxide, and any combination thereof.

22. The method of claim 16, wherein the metal catalyst particle is a M1/M2/Al catalyst, wherein M1 is selected from the group consisting of Cu, Ag, Au, Ru, Rh, Pd, Re, Os, Ir, Pt, and any combination thereof, and wherein M2 is selected from the group consisting of Ti, V, Cr, Mn, Fe, Co, Ni, Zn, a rare earth metal, a La series metal, a Y series metal, and any combination thereof.

23. The method of claim 16, wherein the metal catalyst particle is present at 10 wt % to 90 wt % relative to a total catalyst weight in the acid/metal bifunctional catalyst system.

24. The method of claim 16, wherein the metal catalyst particle is present at 25 wt % to 75 wt % relative to a total catalyst weight in the acid/metal bifunctional catalyst system.

25. The method of claim 16, wherein the acid/metal bifunctional catalyst system further comprises inert particles up to 50 wt % of a total weight of the acid/metal bifunctional catalyst system.

26. The method of claim 16, wherein the mixing comprises:
dry mixing the carbon-coated acid catalyst particle with the metal catalyst particle to produce the acid/metal bifunctional catalyst system.

27. The method of claim 16, wherein the mixing comprises:
mixing the carbon-coated acid catalyst particle with the metal catalyst particle and a binder to form a dough; and
extruding the dough to produce the acid/metal bifunctional catalyst system.

28. The method of claim 16, wherein the mixing comprises:
mixing the carbon-coated acid catalyst particle with the metal catalyst particle and a solvent to form a slurry;
heating the slurry; and
drying the slurry to produce the acid/metal bifunctional catalyst system.

29. The method of claim 16, further comprising:
activating the acid/metal bifunctional catalyst system in hydrogen at 150° C. to 350° C.; and
reacting the activated acid/metal bifunctional catalyst system with a feedstream comprising hydrogen and carbon monoxide.

* * * * *